(12) United States Patent
Tannoury et al.

(10) Patent No.: US 8,936,598 B2
(45) Date of Patent: Jan. 20, 2015

(54) SPINAL DISC PREPARATION TOOL

(75) Inventors: Tony Tannoury, Andover, MA (US); Michael O'Neil, Mansfield, MA (US); Hassan A. Serhan, South Easton, MA (US); Anwar M. Upal, Fall River, MA (US); Michael A. Slivka, Taunton, MA (US); John Riley Hawkins, Cumberland, RI (US)

(73) Assignee: DePuy Synthes Products, LLC, Raynham, MA (US)

( * ) Notice: Subject to any disclaimer, the term of this patent is extended or adjusted under 35 U.S.C. 154(b) by 1168 days.

(21) Appl. No.: 12/353,677

(22) Filed: Jan. 14, 2009

(65) Prior Publication Data
US 2010/0179578 A1  Jul. 15, 2010

(51) Int. Cl.
*A61B 17/32* (2006.01)
*A61B 17/00* (2006.01)

(52) U.S. Cl.
CPC ........ *A61B 17/32* (2013.01); *A61B 2017/00261* (2013.01); *A61B 2017/320064* (2013.01)
USPC ................................ 606/83; 606/79; 606/170

(58) Field of Classification Search
USPC ...................................... 606/170, 79–85, 160
See application file for complete search history.

(56) References Cited

U.S. PATENT DOCUMENTS

| | | | |
|---|---|---|---|
| 2,600,803 A * | 6/1952 | Prather | 433/146 |
| 4,043,343 A * | 8/1977 | Williams | 606/207 |
| 4,369,788 A | 1/1983 | Goald | |
| 4,522,206 A * | 6/1985 | Whipple et al. | 606/174 |
| 4,573,448 A | 3/1986 | Kambin | |
| 5,275,609 A * | 1/1994 | Pingleton et al. | 606/170 |
| 5,286,255 A | 2/1994 | Weber | |
| 5,354,311 A | 10/1994 | Kambin et al. | |
| 5,395,317 A | 3/1995 | Kambin | |
| 5,433,725 A | 7/1995 | Christian et al. | |
| 5,439,464 A | 8/1995 | Shapiro | |
| 5,618,294 A * | 4/1997 | Aust et al. | 606/170 |
| 5,620,415 A | 4/1997 | Lucey et al. | |
| 5,653,713 A * | 8/1997 | Michelson | 606/83 |
| 5,683,359 A | 11/1997 | Farkas et al. | |
| 5,702,420 A | 12/1997 | Sterling et al. | |
| 5,785,647 A | 7/1998 | Tompkins et al. | |

(Continued)

FOREIGN PATENT DOCUMENTS

| | | |
|---|---|---|
| EP | 463798 A1 | 1/1992 |
| EP | 538984 A2 | 4/1993 |

(Continued)

OTHER PUBLICATIONS

International Search Report, PCT/US2010/020722, dated Mar. 22, 2010.

(Continued)

*Primary Examiner* — Matthew Lawson
*Assistant Examiner* — Zade Coley
(74) *Attorney, Agent, or Firm* — Nutter McClennen & Fish LLP

(57) ABSTRACT

A spinal disc preparation tool is provided that includes an elongate shaft having an inner lumen extending therethrough along a longitudinal axis between proximal and distal ends thereof. A lower jaw is located on a distal end of the elongate shaft for receiving tissue and delivering tissue to the inner lumen, and an upper jaw is pivotally movable relative to the lower jaw. The tool can include various features to facilitate removal and/or collection of tissue.

23 Claims, 21 Drawing Sheets

(56) References Cited

U.S. PATENT DOCUMENTS

| | | | |
|---|---|---|---|
| 5,797,939 A | 8/1998 | Yoon | |
| 5,797,958 A | 8/1998 | Yoon | |
| 5,810,826 A * | 9/1998 | .ANG.kerfeldt et al. | 606/80 |
| 5,851,214 A * | 12/1998 | Larsen et al. | 606/170 |
| 5,893,863 A | 4/1999 | Yoon | |
| 5,904,647 A * | 5/1999 | Ouchi | 600/104 |
| 5,919,202 A | 7/1999 | Yoon | |
| 5,922,001 A | 7/1999 | Yoon | |
| 5,922,002 A | 7/1999 | Yoon | |
| 5,984,938 A | 11/1999 | Yoon | |
| 5,984,939 A * | 11/1999 | Yoon | 606/170 |
| 5,997,896 A * | 12/1999 | Carr et al. | 424/426 |
| 6,007,496 A | 12/1999 | Brannon | |
| 6,083,150 A * | 7/2000 | Aznoian et al. | 600/564 |
| 6,939,351 B2 | 9/2005 | Eckman | |
| 7,204,811 B2 | 4/2007 | Kortenbach et al. | |
| 7,375,325 B2 | 5/2008 | Burkhardt et al. | |
| 2002/0107457 A1 * | 8/2002 | Francese et al. | 600/564 |
| 2002/0133148 A1 * | 9/2002 | Daniel et al. | 606/34 |
| 2003/0135218 A1 | 7/2003 | Eckman | |
| 2004/0243157 A1 * | 12/2004 | Connor et al. | 606/159 |
| 2004/0260198 A1 * | 12/2004 | Rothberg et al. | 600/564 |
| 2005/0038439 A1 | 2/2005 | Eckman | |
| 2005/0216019 A1 | 9/2005 | Eckman | |
| 2005/0267503 A1 * | 12/2005 | Hunstad | 606/170 |
| 2005/0273084 A1 | 12/2005 | Hinman et al. | |
| 2006/0167450 A1 * | 7/2006 | Johnson et al. | 606/48 |
| 2006/0167461 A1 * | 7/2006 | Hawkins et al. | 606/90 |
| 2006/0224160 A1 | 10/2006 | Trieu et al. | |
| 2006/0247668 A1 * | 11/2006 | Park | 606/160 |
| 2007/0088362 A1 | 4/2007 | Bonutti et al. | |
| 2007/0191857 A1 | 8/2007 | Allard et al. | |
| 2007/0265633 A1 * | 11/2007 | Moon et al. | 606/83 |

FOREIGN PATENT DOCUMENTS

| | | |
|---|---|---|
| EP | 541377 A1 | 5/1993 |
| EP | 614647 A2 | 9/1994 |
| WO | 9207516 A1 | 5/1992 |
| WO | 9519145 A1 | 7/1995 |
| WO | 9622056 A1 | 7/1996 |
| WO | 9958066 A1 | 11/1999 |
| WO | 02089722 A1 | 11/2002 |

OTHER PUBLICATIONS

M. Pfeiffer et al., Arch Orthop Trauma Surg. (1990) 109:211-216, "Automated percutaneous lumbar discectomy with and without chymopapain pretreatment versus non-automated, discoscopy-monitored percutaneous lumbar discectomy".

Kambin and Savitz, The Mount Sinai Journal of Medicine, vol. 67, No. 4, Sep. 2000, "Arthroscopic MicroDiscectomy: An Alternative to Open Disc Surgery", p. 283-287.

Kambin and Schaffer, "Kambin Arthroscopic Micradiscectomy System", Smith & Nephew Spine, Feb. 1994.

* cited by examiner

B-B

A-A

C-C thru E-E

F-F

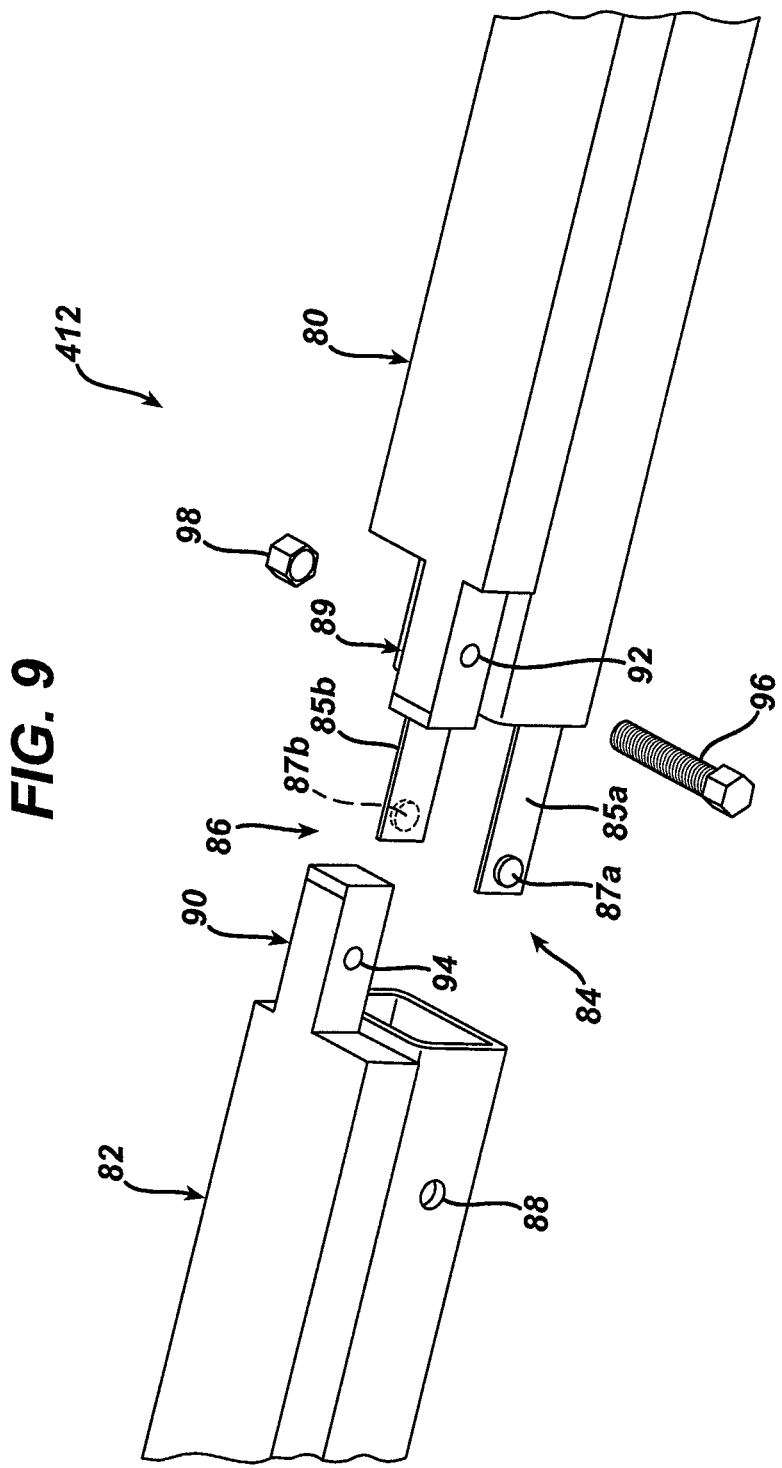

SPINAL DISC PREPARATION TOOL

FIELD OF THE INVENTION

The present invention relates to devices and methods for preparing adjacent vertebrae for a disc replacement.

BACKGROUND OF THE INVENTION

Various physical conditions can manifest themselves in the form of damage or degeneration of an intervertebral disc, the result of which is mild to severe chronic back pain. Intervertebral discs serve as "shock" absorbers for the spinal column, absorbing pressure delivered to the spinal column. Additionally, they maintain the proper anatomical separation between two adjacent vertebra. This separation is necessary for allowing both the afferent and efferent nerves to exit and enter, respectively, the spinal column.

Treatment for a diseased or damaged disc can involve partial or complete removal of the affected disc and implantation of a spinal disc replacement for fusion or non-fusion purposes. A discectomy to remove a spinal disc can involve multiple passes into an out of the disc space between vertebrae, and each one of these passes to remove the disc tissue can increase the risk of nerve injury and contamination of the disc space. In addition, each pass becomes time consuming for the surgeon as there must be a focus with each pass on proper entry into the disc space, removing a portion of tissue, and manually clearing the device of the removed tissue to prepare the device for the subsequent pass into the disc space. During these procedures, it can also be advantageous to prepare the vertebral endplates for the implantation of a disc implant, which is routinely achieved using a separate tool.

Accordingly, there is a need for improved methods and devices for preparing an intervertebral disc space.

SUMMARY OF THE INVENTION

The present invention provides various devices and methods for preparing an intervertebral disc space. In one embodiment, a spinal disc preparation tool is provided and includes an elongate shaft having an inner lumen extending therethrough along a longitudinal axis between proximal and distal ends thereof. A lower jaw is located on a distal end of the elongate shaft for receiving tissue and delivering tissue to the inner lumen, and an upper jaw is pivotally movable relative to the lower jaw. The upper and lower jaws define a tissue-receiving cavity having a maximum cross-sectional area taken transverse to the longitudinal axis that is less than a cross-sectional area of the inner lumen of the elongate shaft taken transverse to the longitudinal axis at a distal opening of the inner lumen. For example, the cross-sectional area of the tissue-receiving cavity can be about 50% less than the cross-sectional area of the inner lumen at the distal opening of the inner lumen. In one exemplary embodiment, the inner lumen has a cross-sectional area taken transverse to the longitudinal axis that increases from the distal opening to a proximal end of the inner lumen, and for example, the cross-sectional area at the proximal end of the inner lumen can be about twice the cross-sectional area at the distal opening of the inner lumen. In another exemplary embodiment, the upper and lower jaws can be removably and replaceably coupled to the elongate shaft.

The upper and lower jaws can also include features to facilitate aspiration of the tissue. In one embodiment, at least one of the jaws includes one or more holes formed therein for allowing gas and/or fluid to pass therethrough to aid in aspiration of cut tissue through the inner lumen. At least one of the jaws can also include an inner surface having a coating for aiding in aspiration of cut tissue through the inner lumen. For example, the coating can be hydrophilic and provide a lubricated surface within at least one of the jaws, or the coating can be hydrophobic such that the coating repels fluid and prevents adhesion of cut tissue to the upper jaw and/or lower jaw. In another embodiment, a septum can be formed in the lower jaw and it can be configured to separate cut tissue into two portions. In other aspects, the lower jaw can be removably and replaceably coupled to the elongate shaft. The upper and lower jaws can also include features to prepare the area surrounding the spinal disc, such as at least one bone cutting element that can be formed on at least one of the upper and lower jaws. In another embodiment, the upper jaw can have a width that is equal or greater to a width of the lower jaw.

In other embodiments, the tool can include a handle coupled to a proximal end of the elongate shaft and having an actuator operatively associated with the upper jaw for pivoting the upper jaw relative to the lower jaw. An aspiration hole can be formed in the handle and it can be in fluid communication with the inner lumen. In one embodiment, the aspiration hole is positioned such that the aspiration hole is blocked by the actuator when the actuator is actuated. The tool can also include a tissue collection chamber in fluid communication with the inner lumen and configured to separate cut tissue from fluid. The tool can include other features as well, such as an articulation joint formed in the shaft for allowing angular orientation of the distal end of the shaft.

In another embodiment, a spinal disc preparation tool is provided and includes an elongate shaft having an inner lumen extending therethrough along a longitudinal axis between proximal and distal ends thereof, and upper and lower jaws disposed on a distal end of the elongate shaft. The upper jaw is movable relative to the lower jaw to cut tissue therebetween and deliver tissue to the inner lumen of the elongate shaft. At least one of the upper and lower jaws is removably and replaceably coupled to the elongate shaft. In one embodiment, the upper jaw can include a removable hood or a removable insert having a blade thereon for cutting tissue. In another exemplary embodiment, the upper and lower jaws can be coupled to a distal portion of the elongate shaft, and the distal portion of the elongate shaft can be removably coupled to a proximal portion of the elongate shaft such that the distal portion of the elongate shaft and the upper and lower jaws are removable and replaceable.

In another embodiment, a spinal disc preparation tool is provided and includes an elongate shaft having an inner lumen extending therethrough between proximal and distal ends thereof, and upper and lower jaws located on the distal end and movable relative to one another for cutting tissue. A tissue collector is coupled to the proximal end of the elongate shaft and is in fluid communication with the inner lumen such that the tissue collector is effective to collect tissue cut by the upper and lower jaws. In one exemplary embodiment, the tissue collector can include a housing having a collecting module disposed therein and configured to separate cut tissue from fluid. The collecting module can include indicia to measure the amount of cut tissue. The collecting module can have a variety of configurations, and it can be configured to collect cut tissue therein, or to collect cut tissue on an external surface thereof. In one embodiment, the collecting module can be a mesh bag. The tissue collector can be removably coupled to the elongate shaft. The upper and lower jaws can also include additional features. For example, at least one aspirating hole in fluid communication with the inner lumen can be formed in at least one of the upper jaw, the lower jaw, and the elongate shaft. At least one tissue cutting surface feature can also be formed on at least one of the upper and lower jaws.

In another embodiment, a spinal disc preparation tool is provided and includes an elongate shaft having an inner lumen extending therethrough between proximal and distal ends thereof, and a lower jaw associated with a distal end of the elongate shaft. An upper jaw is movably coupled to the distal end of the elongate shaft and it is adapted to move relative to the lower jaw to cut tissue. At least one tissue cutting surface feature is formed on at least one of the upper and lower jaws. The tissue cutting surface feature can be configured in a variety of ways, such as to remove tissue along a surface of a vertebral endplate or to cut into a surface of an endplate. The surface feature can also be formed in a number of ways. For example, the at least one tissue cutting surface feature can be in the form of a rasp formed on an exterior surface of the lower jaw, a curette formed on an exterior surface of the lower jaw, a tooth formed on opposed sides of the upper and lower jaws, or a protrusion formed on an exterior surface of the lower jaw and having a concavity for scraping tissue.

Methods for cutting tissue are also provided, and in one embodiment the method can include inserting a distal end of an elongate shaft of a spinal disc preparation tool between adjacent vertebrae, and actuating an upper jaw on the distal end of the elongate shaft to move the upper jaw relative to a lower jaw on the distal end of the elongate shaft to cut tissue between the adjacent vertebrae. The cut tissue is aspirated through an inner lumen extending through the elongate shaft, and the tissue is separated from fluid and collected by a tissue collector in fluid communication with the inner lumen.

BRIEF DESCRIPTION OF THE DRAWINGS

The invention will be more fully understood from the following detailed description taken in conjunction with the accompanying drawings, in which:

FIG. 9 is a perspective view of one embodiment of a portion of an elongate shaft for use with a spinal disc preparation tool having a removable and replaceable distal end showing upper and lower attachment means to couple proximal and distal portions of the upper pusher and the lower tube together;

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Figure 1:
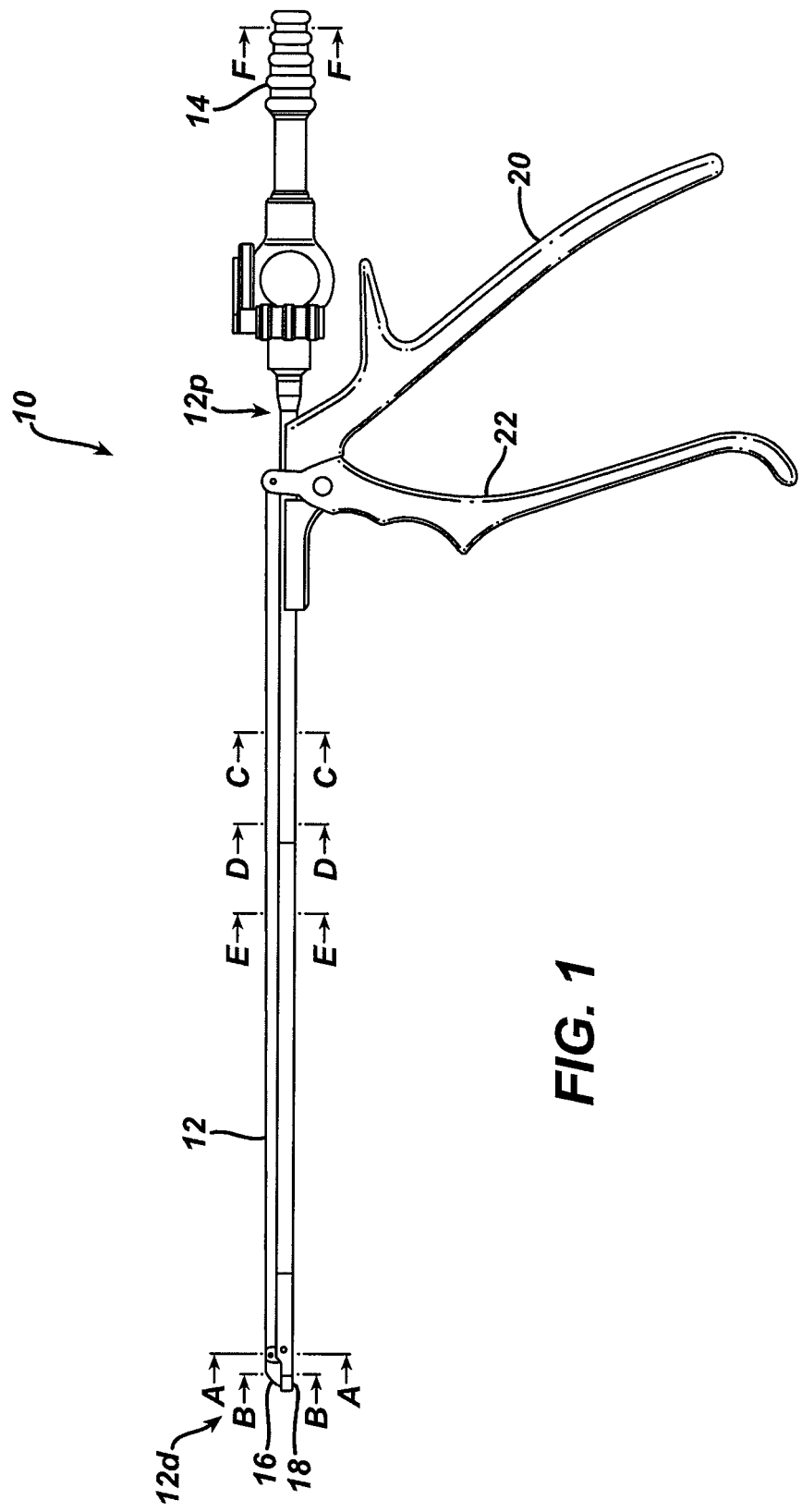
FIG. 1 is a side view of a spinal disc preparation tool having a distal end with upper and lower jaws for cutting tissue.

The present invention provides various methods and devices for preparing an intervertebral disc space. A person skilled in the art will appreciate that the methods and devices described herein can also be used for the removal of soft tissue, muscle, fascia, or ligaments prior to entering the disc space. In general, a spinal disc preparation tool is provided that is adapted to cut tissue between an upper and lower jaw at a distal end of the tool. FIG. 1 illustrates one exemplary embodiment of a spinal disc preparation tool 10 that generally includes an elongate shaft 12 having an inner lumen extending therethrough along a longitudinal axis between a proximal end 12$p$ and a distal end 12$d$ of the elongate shaft 12. The elongate shaft 12 includes upper and lower jaws 16, 18 associated with the distal end 12$d$ thereof, and a port 14 associated with the proximal end 12$p$ thereof that is adapted to facilitate aspiration of tissue through the inner lumen of the elongate shaft 12. In one embodiment, the lower jaw 18 can be located on or formed in the distal end 12$d$ of the elongate shaft 12, and the upper jaw 16 can be movably coupled to the distal end 12$d$ of the elongate shaft 12 to allow the upper jaw 16 to move relative to the lower jaw 18 to cut tissue therebetween, for example, with a shearing motion. The upper and lower jaws 16, 18 can define a tissue-receiving cavity therebetween for receiving the cut tissue.

Figure 2:
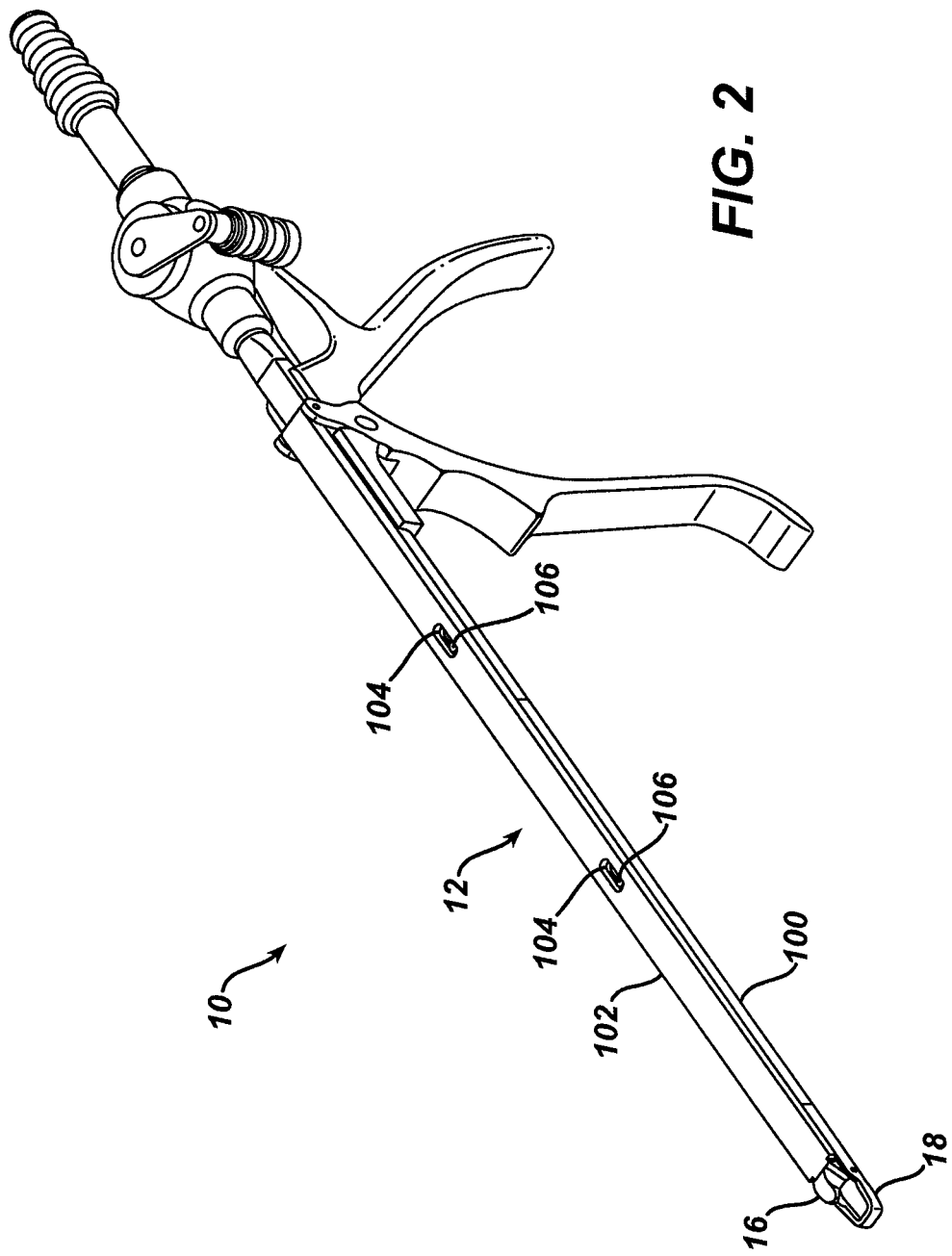
FIG. 2 is a perspective view of the spinal disc preparation tool of FIG. 1 showing an upper pusher coupled to the upper jaw and a lower tube coupled to the lower jaw.

The elongate shaft 12 can have a variety of configurations, and it can be rigid or flexible depending on the intended use. In an exemplary embodiment, the elongate shaft 12 is adapted to be positioned within a body cavity and thus can have a length sufficient to allow the distal end 12$d$ of the shaft 12 to be positioned within the body while the proximal end 12$p$ remains external to the body to allow a user to grasp a handle 20 and operate an actuator 22 extending from the proximal end 12$p$ of the elongate shaft 12. While the elongate shaft 12 can be formed from a single shaft having the inner lumen disposed therethrough, the elongate shaft 12 can also optionally be formed from a lower tube 100 having an inner lumen disposed therethrough and the lower jaw 18 disposed on a distal end thereof, and an upper pusher 102 having the upper jaw 16 disposed on a distal end thereof. The upper pusher 102 can be configured to move back and forth longitudinally along the lower tube 100 to open and close the upper jaw 18 to cut tissue. The lower tube 100 and the upper pusher 102 can be coupled in a variety of ways. For example, the upper pusher 102 can include a plurality of slots 104 formed therein that receive a plurality of pins 106 formed on the lower tube. In the illustrated embodiment shown in FIG. 2, the upper pusher 102 and the lower tube 100 include two slots 104 and two pins 106, respectively. The pins 106 are configured to sit within the slots 104 to couple the upper pusher 102 and the lower tube 100 together, but the pins 106 can also slide longitudinally within the slots 104 to allow the upper pusher 102 to move relative to the lower tube 100 to cause the upper jaw 18 to pivot relative to the lower jaw 18 in order to cut tissue, as will be discussed in more detail below. One skilled in the art will appreciate that the elongate shaft 12 can be made from a variety of biocompatible materials that have properties sufficient to enable the shaft 12 to be inserted and moved within the body.

Figure 3:
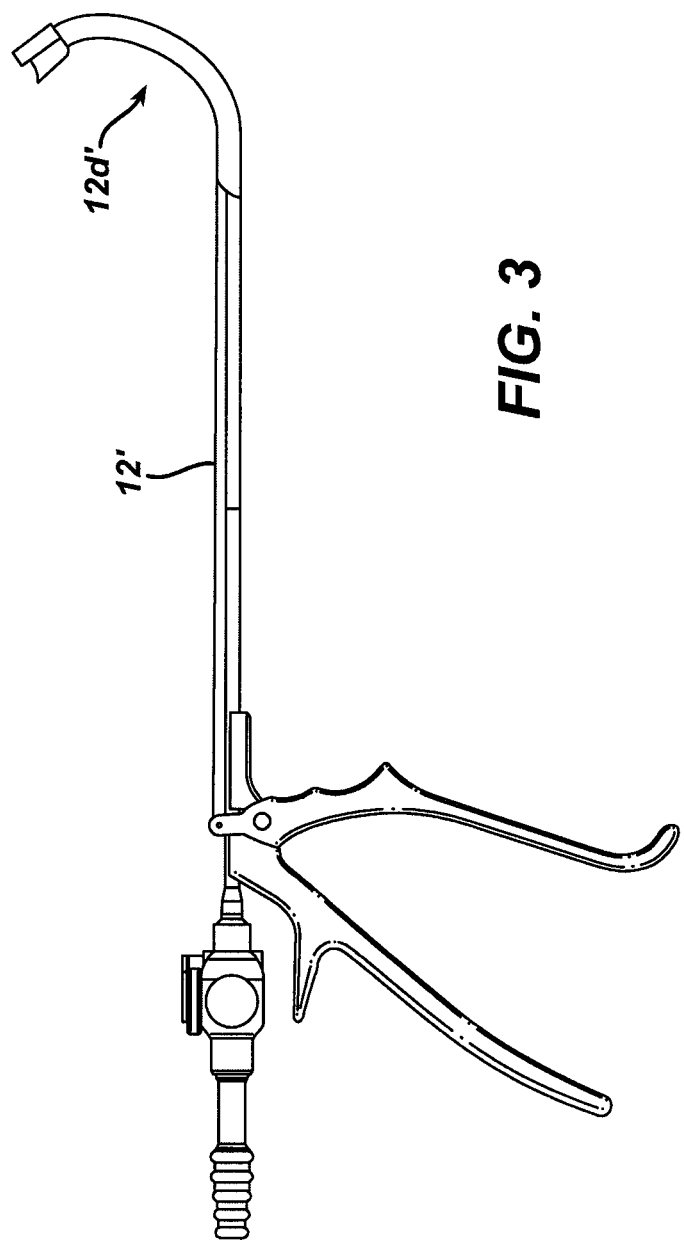
FIG. 3 is a side view of another embodiment of a spinal disc preparation tool having an elongate shaft with a pre-bent distal end.
Figure 4A:
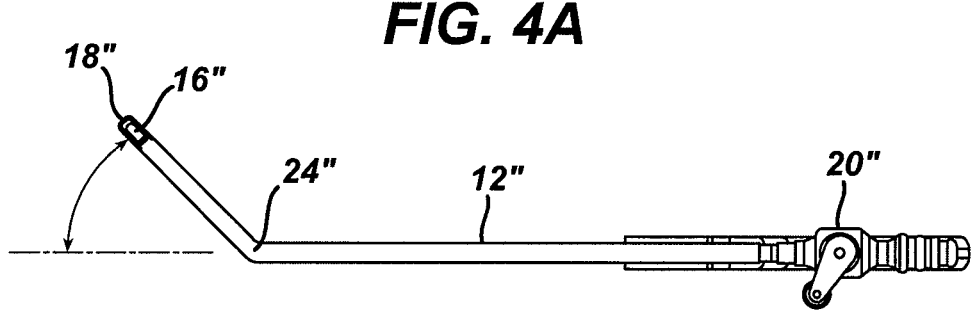
FIG. 4A is a side view of another embodiment of a spinal disc preparation tool having an elongate shaft with a distal portion that articulates.
Figure 4B:
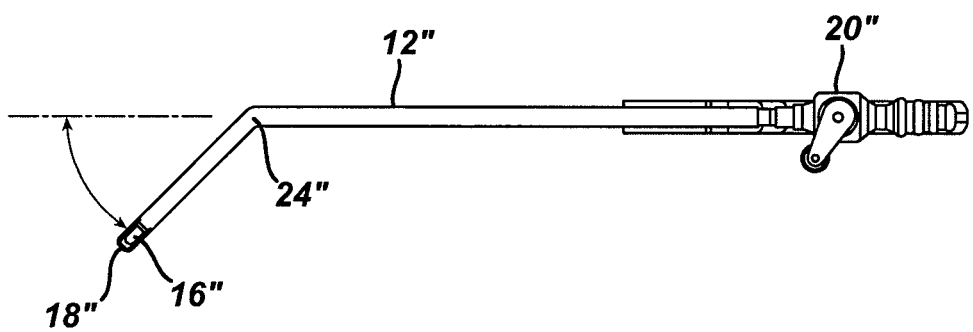
FIG. 4B is a side view of another embodiment of a spinal disc preparation tool having an elongate shaft with a distal portion that articulates.

The elongate shaft 12 can optionally include features to allow a distal portion of the elongate shaft 12 to reach a contralateral side of the vertebral disc space. In one embodiment, the distal end 12$d'$ of the elongate shaft 12' can be pre-bent to form an arc, as shown in FIG. 3. The distal end 12$d'$ of the elongate shaft 12' can be arced in a variety of directions, but in the illustrated embodiment the distal end 12$d'$ is arced such that it resides in substantially the same plane as the handle 20 of the tool 10. In another embodiment, the elongate shaft can include features to allow a distal portion of the elongate shaft to articulate to redirect the distal portion of the elongate shaft. In one exemplary embodiment as shown in FIGS. 4A-4B, the elongate shaft 12" can include an articulation joint 24" formed therein at a location proximal to the upper and lower jaws 16", 18". The articulation joint 24" can allow the portion of the elongate shaft 12" distal to the joint 24" to pivot side-to-side along a single plane, or in other embodiments along multiple planes, relative to the portion of the elongate shaft 12" proximal to the joint 24". Articulation can be controlled by a trigger, knob, or other actuation mechanism on the handle 20", or actuation can be passively controlled by applying a force to the distal portion, e.g., with tissue. A person skilled in the art will appreciate that various articulation mechanisms known in the art can be used to allow articulation of the distal portion of the elongate shaft. While not shown, the elongate shaft can also optionally be configured to rotate relative to the handle, and various rotation mechanisms known in the art can be used.

Figure 5A:
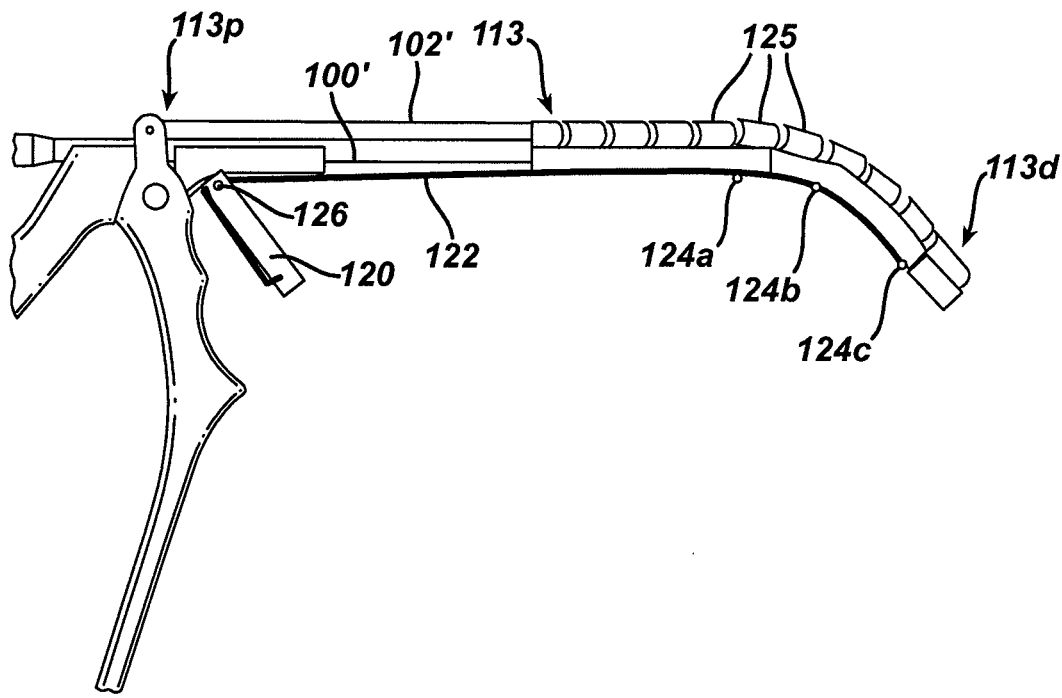
FIG. 5A is a side view of another embodiment of a spinal disc preparation tool having an elongate shaft with a distal portion that is flexible.
Figure 5B:
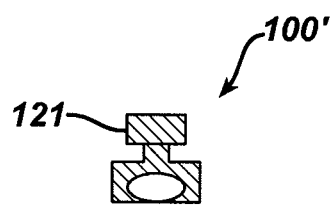
FIG. 5B is a cross-sectional view of a lower tube of the elongate shaft of FIG. 5A.
Figure 5C:
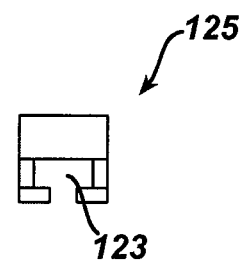
FIG. 5C is a side view of a pusher member of an upper pusher of the elongate shaft of FIG. 5A.

In another exemplary embodiment shown in FIGS. 5A-5C, the distal portion of the elongate shaft can be flexible. For example, the lower tube 100' of the elongate shaft 113 can include a plurality of male connectors 121 configured to couple to a plurality of female connectors 123 formed on the upper pusher 102'. The upper pusher 102' can be formed from a plurality of individual pusher members 125 with each pusher member 125 having a single female connector 123 formed thereon to connect to the male connectors 121 of the lower tube 100'. The use of individual pusher members 125 allows the upper pusher 102' to bend during articulation as gaps can form between the individual pusher members 125. The articulation of the distal portion 113$d$ of the elongate shaft 113 can be controlled by an actuation member disposed on the proximal end 113$p$ of the elongate shaft 113, such as a lever 120 shown in FIG. 5A. A person skilled in the art will appreciate that the actuation member can have any configuration or shape that is capable of controlling the articulation of the distal portion 113d of the elongate shaft 113. In one exemplary embodiment, one or more guidewires 122 can extend from attachment portions on the distal portion of the elongate shaft 113 to the lever 120. In the illustrated embodiment shown in FIG. 5A, there are three attachment points 124a, 124b, 124c that attach the guidewire 122 to the distal portion of the elongate shaft 113. The lever 120 can pivot about a pivot pin 126 disposed through the lever 120, causing tensioning and/or relaxing of the guidewire 122 to articulate the distal portion of the elongate shaft 113.

The upper and lower jaws 16, 18 associated with the distal end 12d of the elongate shaft 12 can also have a variety of configurations. In the illustrated embodiment, the lower jaw 18 has a generally elongate shape that extends distally from the distal end 12d of the elongate shaft 12. The lower jaw 18 can be formed from a concavity formed in the elongate shaft 12 that is adapted to receive cut tissue, or the lower jaw 18 can be a separate component that is fixedly or removably attached to the distal end 12d of the elongate shaft 12. A person skilled in the art will appreciate that the lower jaw 18 can be attached to the elongate shaft 12 in any manner that allows the lower jaw 18 to remain fixed relative to the elongate shaft 12 during cutting of tissue. In other embodiments, the upper and/or lower jaws 16, 18 can be removable and replaceable to allow jaws having various configurations to be selectively attached to the tool 10, as will be discussed in more detail below.

The upper jaw 16 can be pivotally coupled to the distal end 12d of the elongate shaft 12 and/or to the lower jaw 18, and it can be adapted to pivot relative to the lower jaw 18 and the elongate shaft 12 in order to cut tissue. The upper jaw 16 can have a variety of configurations, but in the illustrated embodiment the upper jaw 16 has a generally elongate shape with a concavity formed therein for receiving the cut tissue. The concave configuration of the upper and lower jaws 16, 18 together can form a tissue-receiving cavity that is configured to receive the cut tissue. The tissue-receiving cavity can have a variety of configurations, but in the illustrated embodiment is generally in the form of a oval-shaped cavity between the upper and lower jaws 16, 18.

Figure 6A:
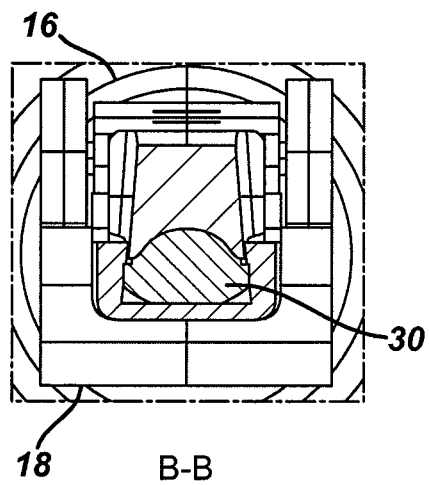
FIG. 6A is a cross-sectional view taken along line B-B of the distal end of a tissue-receiving cavity defined by the upper and lower jaws shown in FIG. 1.
Figure 6B:
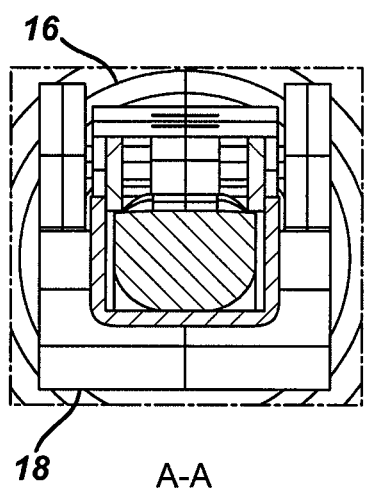
FIG. 6B is a cross-sectional view taken along line A-A of the distal opening of an inner lumen defined by an elongate shaft of the tool shown in FIG. 1.
Figure 6C:
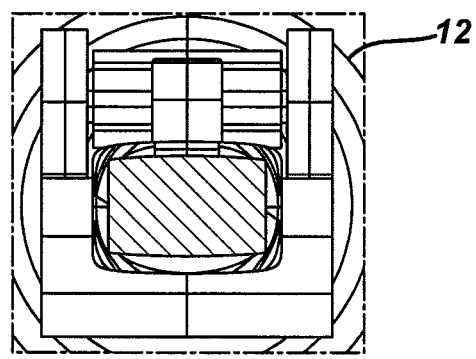
FIG. 6C is a cross-sectional view taken along lines C-C, D-D, and E-E of the inner lumen of the elongate shaft shown in FIG. 1.
Figure 6D:
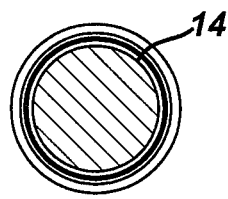
FIG. 6D is a cross-sectional view taken along line F-F of a proximal opening of the inner lumen of the elongate shaft shown in FIG. 1.

One exemplary embodiment of a tissue-receiving cavity 30 defined between the upper and lower jaws 16, 18 is illustrated in FIG. 6A. The cross-sectional area of the tissue-receiving cavity 30 can be chosen in order to improve the aspiration of the cut tissue. In one exemplary embodiment, as shown in FIG. 6A, the tissue-receiving cavity 30 can have a maximum cross-sectional area that is less than a cross-sectional area of the inner lumen of the elongate shaft 12, at least at the distal opening of the inner lumen shown in FIG. 6B. The reduced cross-sectional area of the tissue-receiving cavity can control the size of the cut tissue therein and thus the size of the tissue that passes into the inner lumen. Such a configuration can thus improve aspiration by ensuring that the cut tissue has a size that is less than the size of the inner lumen to allow the tissue to easily fit within the inner lumen. In certain exemplary embodiments, the cross-sectional area of the tissue-receiving cavity 30 can be about 50% less than the cross-sectional area of the inner lumen at the distal opening of the inner lumen. A person skilled in the art will appreciate, however, that the cross-sectional area of the tissue-receiving cavity 30 can be any amount less than the cross-sectional area of the inner lumen to improve aspiration of the cut tissue. Additionally, the cross-sectional area of the inner lumen can increase from the distal end to the proximal end of the inner lumen, as shown in FIG. 6C, to also improve aspiration of the cut tissue by increasing the size of the inner lumen as the tissue moves proximally through the tool 10. For example, the cross-sectional area at the proximal end of the inner lumen can be about twice the cross-sectional area of the distal end of the inner lumen. A person skilled in the art will appreciate, however, that any increase in the cross-sectional area of the inner lumen from the distal end to the proximal end thereof will act to increase the effectiveness of the aspiration of the cut tissue through the inner lumen. FIG. 6D illustrates the cross-sectional area of the proximal end of the tool, which is preferably large enough to accommodate the cut tissue received from the inner lumen of the elongate shaft 12.

Figure 7A:
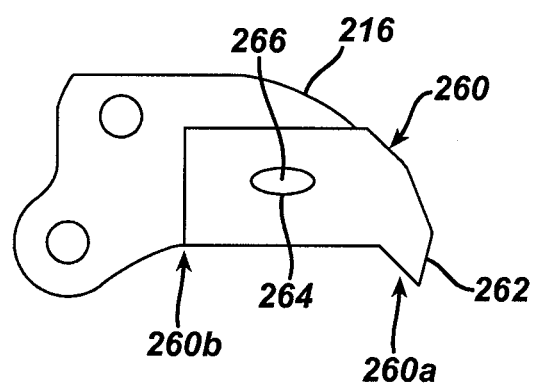
FIG. 7A is a side view of another embodiment of an upper jaw for use with a spinal disc preparation tool, the jaw having a removable and replaceable hood with a blade coupled to an outer surface thereof.
Figure 7B:
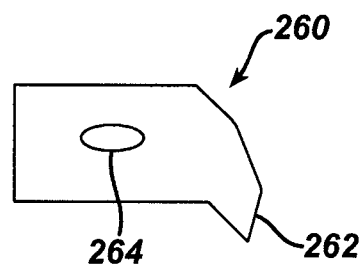
FIG. 7B is a side view of the hood of FIG. 7A.

As discussed above, the upper and lower jaws 16, 18 can also be removable and replaceable to facilitate cutting tissue therebetween. For example, the upper jaw 16 and/or the lower jaw 18 can include removable and/or disposable cutting blades such that the blades can be removed from the upper jaw 16 and/or lower jaw 18 and replaced after multiple uses have dulled the sharpness of the blades to facilitate cutting tissue. In one exemplary embodiment, shown in FIGS. 7A-7B, the upper jaw 216 includes a removable hood 260 that has an elongate concave shape that is sized and shaped to fit around an outer surface of the upper jaw 216. The hood 260 includes a blade 262 formed on a first end 260a thereof that is adapted to cut tissue. The hood 260 can be configured to couple to the upper jaw 216 in a variety of ways, but in the illustrated embodiment the hood 260 includes first and second openings 264 formed on opposed sides of a second end 260b of the hood 260 that correspond to first and second protrusions 266 formed on opposed sides of the upper jaw 216. The first and second openings 264 are configured to removably receive the first and second protrusions 266 of the upper jaw 216 to removably couple the hood 260 to the upper jaw 216. A person skilled in the art will appreciate, however, that the hood 260 can be coupled to the outer surface of the jaw using any technique known in the art. Moreover, a person skilled in the art will appreciate that the lower jaw can also include a removable hood with a cutting blade configured to fit around an outer surface of the lower jaw, used alone or in combination with the hood 260 on the upper jaw 216.

Figure 8A:
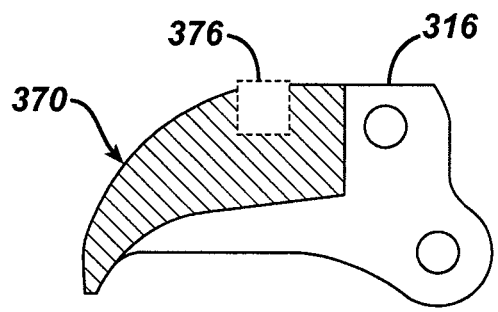
FIG. 8A is a side view of another embodiment of an upper jaw for use with a spinal disc preparation tool, the jaw having a removable and replaceable insert with a blade coupled to an inner surface thereof.
Figure 8B:
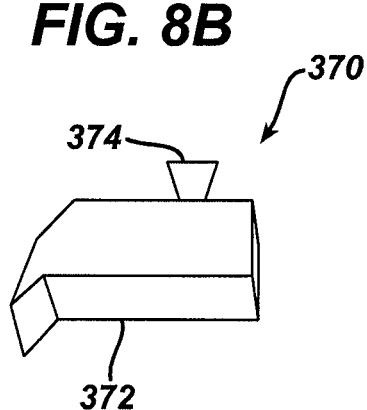
FIG. 8B is a side view of the insert of FIG. 8A.
Figure 8C:
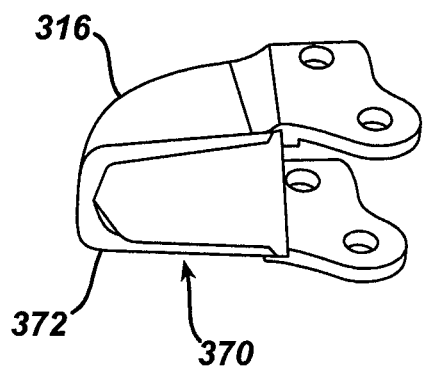
FIG. 8C is a perspective view of the insert positioned within the upper jaw of FIG. 8A.

In another exemplary embodiment, shown in FIGS. 8A-8C, the upper jaw 316 can include a removable insert 370 that has an elongate concave shape that is sized and shaped to fit in an inner surface of the upper jaw 316. The insert 370 includes a blade 372 formed along a lower edge thereof that is configured to cut tissue. The insert 370 can be configured to couple to the inner surface of the upper jaw 316 in a variety of ways, but in the illustrated embodiment the insert 370 includes a protrusion 374 that is configured to fit within an opening 376 formed in the inner surface of the upper jaw 316. The protrusion 374 and the opening 376 can couple together in a variety of ways. For example, the protrusion 374 can be tapered such that the end of the protrusion 374 that is attached to the insert 370 is narrower than the end that is inserted into the opening 376 in the upper jaw 316. The protrusion 374 can be press-fit into the opening 376 such that the protrusion 374 deforms upon insertion into the opening 376, and then once fully inserted returns to its original state whereby the protrusion 374 extends into the opening 376 and the wider end of the tapered protrusion 374 holds the protrusion 374 within the opening 376. A person having ordinary skill in the art will appreciate that a variety of mechanisms can be used to secure the protrusion 374 of the insert 370 within the opening 376 formed in the upper jaw 316, and that any number of corresponding protrusions and openings can be used. Moreover, a person skilled in the art will appreciate that the lower jaw can also include a removable insert with a cutting blade configured to fit in an inner surface of the lower jaw, used alone or in combination with the insert 370 in the inner surface of the upper jaw 316.

In yet another exemplary embodiment, shown in FIG. 9, a distal portion of the elongate shaft 412 and the upper and lower jaws can be removable and replaceable. While the removable distal portion 80 of the elongate shaft 412 can be coupled to the proximal portion 82 of the elongate shaft 412 in a variety of ways, in the illustrated embodiment a lower attachment means 84 is configured to couple the proximal and distal portions 80, 82 of the lower tube of the elongate shaft 12, and an upper attachment means 86 is configured to couple the proximal and distal portions 80, 82 of the upper pusher of the elongate shaft 412. The lower and upper attachment means 84, 86 can have various configurations, but in the embodiment shown in FIG. 9, the lower attachment means 84 is in the form of first and second arms 85a, 85b extending from the proximal end of the distal portion 80 of the lower tube along the longitudinal axis thereof. The arms 85a, 85b include first and second protrusions 87a, 87b formed on the outer surfaces of the arms 85a, 58b. The proximal portion 82 of the lower tube includes first and second holes 88 formed in opposed lateral sides thereof that are configured to receive the protrusions 87a, 87b of the arms 85a, 85b of the distal portion 80 of the lower tube. The holes 88 are positioned along the proximal portion of the lower tube such that the proximal end of the distal portion of the lower tube abuts the distal end of the proximal portion of the lower tube when the protrusions 87a, 87b of the arms 85a, 85b are inserted into the holes 88. To couple the portions of the lower tube, the arms 85a, 85b are pressed towards one another and inserted into the distal end of the proximal portion of the lower tube. The arms 85a, 85b of the distal portion of the lower tube are pushed into the proximal portion of the lower tube until the protrusions 87a, 87b reach and move into the holes 88, thus temporarily locking the portions of the lower tube together. To remove the distal portion of the lower tube, the protrusions 87a, 87b are pressed into the holes 88 and the distal portion of the lower tube is moved distally until the arms 85a, 85b are free from the proximal portion of the lower tube. The upper attachment means 86 is in the form of a first arm 89 extending from the distal portion of the upper pusher and a second arm 90 extending from the proximal portion of the upper pusher. The first and second arms 89, 90 each have a bore 92, 94 formed therethrough such that when the first and second arms 89, 90 are lined up adjacent one another, the bores 92, 94 line up to form a single bore through both the first and second arms 89, 90. A locking mechanism, such as a screw 96, can be inserted through the bores 92, 94 and locked to the first and second arms 89, 90 using a locking nut 98. To remove the distal portion of the upper pusher, the locking nut 98 is unscrewed from the locking mechanism and the locking mechanism is removed from the bores 92, 94 of the first and second arms 89, 90 to allow the first and second arms 89, 90 to be separated.

Figure 10:
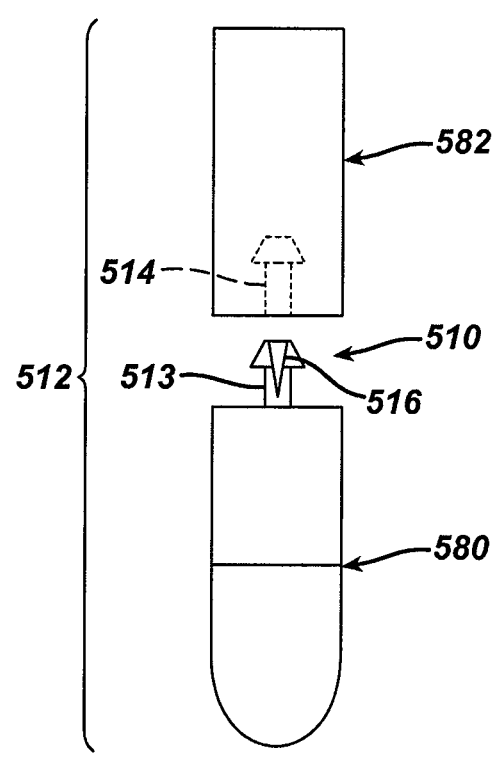
FIG. 10 is a top view of another embodiment of a portion of an elongate shaft for use with a spinal disc preparation tool showing a removable and replaceable distal end.

In another exemplary embodiment shown in FIG. 10, the upper and lower attachment means can be in the form of connectors 510 configured to couple the proximal and distal portions 580, 582 of the elongate shaft 512. In the illustrated embodiment, the distal portion 580 includes a connector 513 in the form of an elongate protrusion extending from a proximal end of the distal portion 580 and having an enlarged head on a proximal end thereof. The connector 513 can be removably disposed within a corresponding bore 514 formed in the proximal portion 582 of the elongate shaft 512. The bore 514 can have a shape that corresponds to the shape of the connector 513 to allow the connector 513 to be inserted to and removably couple thereto. The connector 513 can have a slot or cut-out 516 formed therein that allows the connector 513 to deform upon insertion into the bore 514 and to expand once fully inserted to engage the bore 514. To remove the connector 513 from the bore 514, tension or rotation can be applied to overcome the snap-fit between the connector 513 and the bore 514. A person skilled in the art will appreciate, however, that any type of removable connection between the proximal and distal portions of the elongate shaft can be used to removably and replaceably mate the distal portion to the proximal portion.

Referring back to FIGS. 1 and 2, as indicated above, the proximal end 12p of the elongate shaft 12 can include a handle 20 coupled thereto. The handle 20 can have any shape and size, but it is preferably adapted to facilitate grasping and manipulation of the tool 10. The handle 20 can include an actuator coupled thereto that can have a variety of configurations to control movement of the upper jaw 16 relative to the lower jaw 18. In one embodiment, the actuator 22 is a trigger that is pivotally coupled to the housing 20 and that is operatively connected to a proximal end of the upper pusher 102. A distal end of the upper pusher 102 is coupled to a proximal end of the upper jaw 16, for example, using one or more pivot pins to couple the upper jaw 16 and the upper pusher 102 together to allow the upper jaw 16 is to pivot relative to the upper pusher 102 and the lower tube 100. In the illustrated embodiment, the actuator 22 pivots about a pivot point toward and away from the handle 20 to move the upper pusher 102 proximally and distally. Movement of the actuator 22 towards the handle 20 causes the upper pusher 102 to move distally and push the upper jaw 16 distally, causing the upper jaw 16 to pivot relative to the lower jaw 18 and cut tissue therebetween. Releasing the actuator 22 causes the upper pusher 102 to move proximally and pull the upper jaw 16 proximally, causing the upper jaw 16 to pivot away from the lower jaw 18. A person skilled in the art will appreciate that the actuator 22 can be operatively associated with the upper jaw 16 in any form that facilitates the movement of the upper jaw 16. While the illustrated embodiment shows the actuator 22 in the form of a trigger, a person skilled in the art will appreciate the actuator 22 can have a variety of configurations, including but not limited to a button, a knob, a switch, or any other member that can be adapted to facilitate movement of the upper jaw 16. While not shown, a spring can optionally be used to bias the actuator 22, either toward and or away from the handle 20. For example, movement of the actuator 22 can cause a spring disposed in the handle 20 to compress and move the upper pusher 102 distally to move the upper jaw 16 towards the lower jaw 18 by pushing the upper jaw 16 distally. Releasing the actuator 22 can cause the spring to release and move the upper pusher 102 proximally to move the upper jaw 16 away from the lower jaw 18 by pulling the upper jaw 16 proximally and pivoting the upper jaw 16 away from the lower jaw 18.

Figure 11:
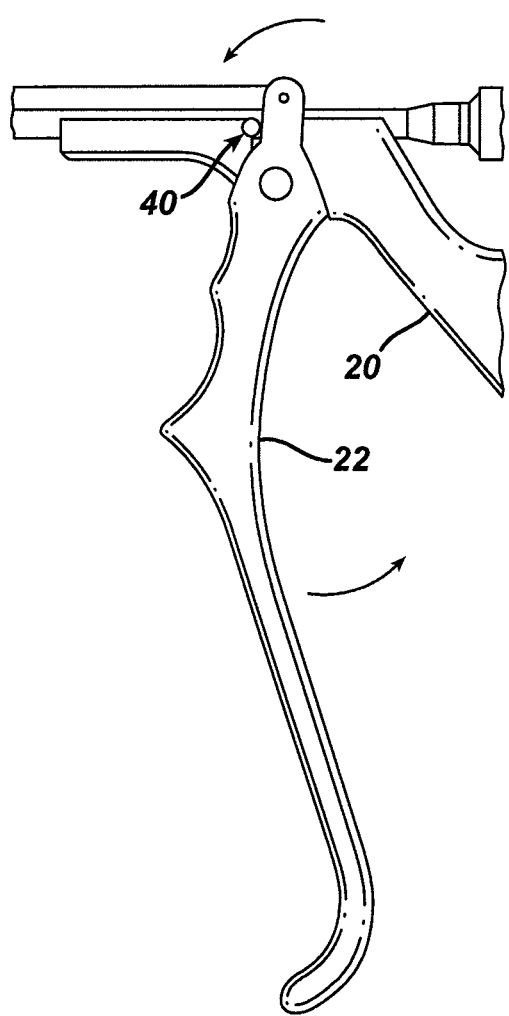
FIG. 11 is a side view of a portion of a handle of the tool of FIG. 1 having one embodiment of an aspiration hole formed therein.
Figure 12A:
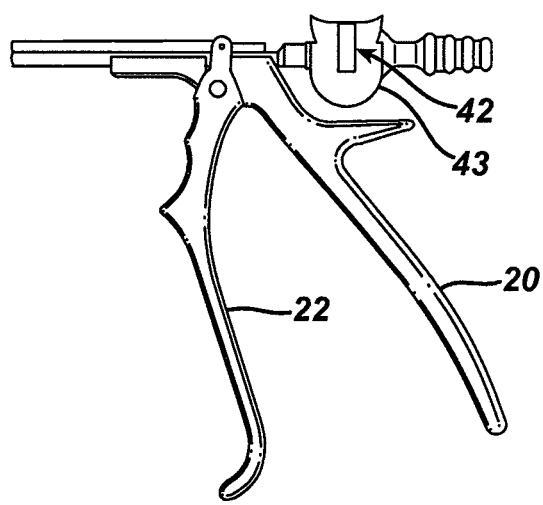
FIG. 12A is a side view of a portion of a handle of the tool of FIG. 1 showing another embodiment of an aspiration hole formed therein.
Figure 12B:
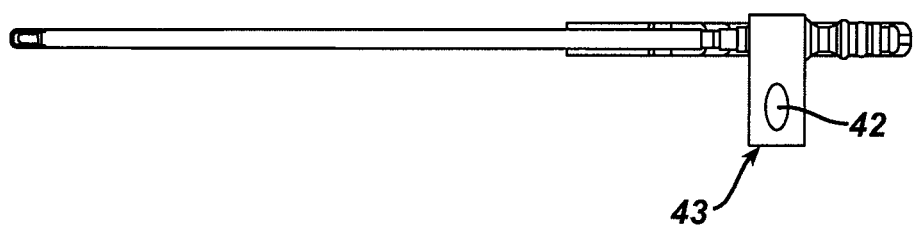
FIG. 12B is a top view of the tool of FIG. 12A showing the aspiration hole formed therein.

The tool 10 can include various additional features to aid in the aspiration of the cut tissue. In one exemplary embodiment, the handle 20 can include one or more aspiration holes formed therein and in fluid communication with the inner lumen of the elongate shaft 12. The aspiration hole can aid in aspiration of the tissue through the inner lumen of the elongate shaft 12 by helping to facilitate the formation of a vacuum within the inner lumen and thus increase the effectiveness of the aspiration when the aspiration hole is blocked. The aspiration hole can be located in a variety of positions on the handle 20. In one exemplary embodiment shown in FIG. 11, the aspiration hole 40 can be located on the handle 20 such that when the actuator 22 is unactivated the hole remains open, and when the actuator 22 is activated the hole is blocked. For example, in the illustrated embodiment the aspiration hole 40 is positioned on the handle 20 at a location just distal to a proximal end of the actuator 22. As the actuator 22 is actuated, the proximal end of the actuator 22 will move distally to block the aspiration hole 40. In another exemplary embodiment, shown in FIGS. 12A-12B, an aspiration hole 42 can be located on the handle 20 in a position that allows the user to block the aspiration hole 42 manually, for example, with a portion of the user's hand, such as a finger. For example, the aspiration hole 42 can be located on a housing 43 in communication with the inner lumen and formed on the tool 10 at a location adjacent to the handle 20 to allow the hole 42 to be covered manually while grasping the handle 20. While FIGS. 11-12B illustrate a single aspiration hole 40, 42, a person skilled in the art will appreciate that any number of aspiration holes can be formed in the handle 20 or anywhere along the length of the tool 10 as long as they can be blocked with a component of the tool 10 or manually by the user. In addition, a person skilled in the art will also appreciate that the tool 10 can include multiple aspiration holes and the aspiration hole(s) can have any size and shape as long as it can be blocked with a component of the tool 10 or manually by the user.

Figure 13:
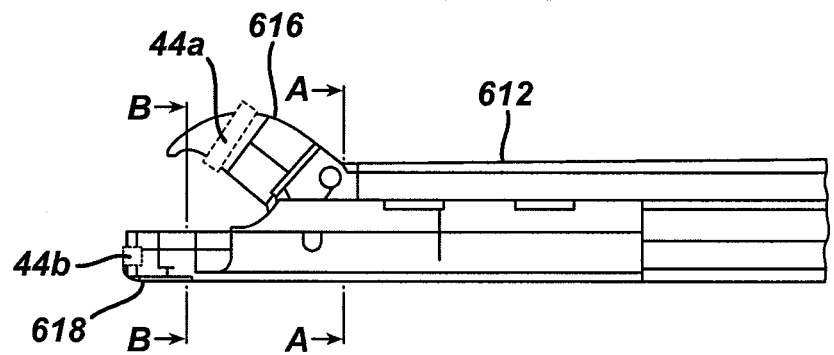
FIG. 13 is a side view of upper and lower jaws of the tool of FIG. 1 with a single aspiration hole in each of the upper and lower jaws.
Figure 14A:
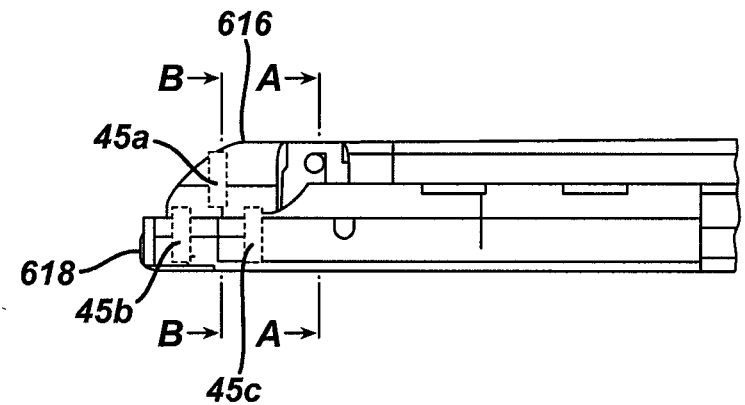
FIG. 14A is a side view of upper and lower jaws of the tool of FIG. 1 with a single aspiration hole in the upper jaw and multiple aspiration holes in the lower jaw.
Figure 14B:
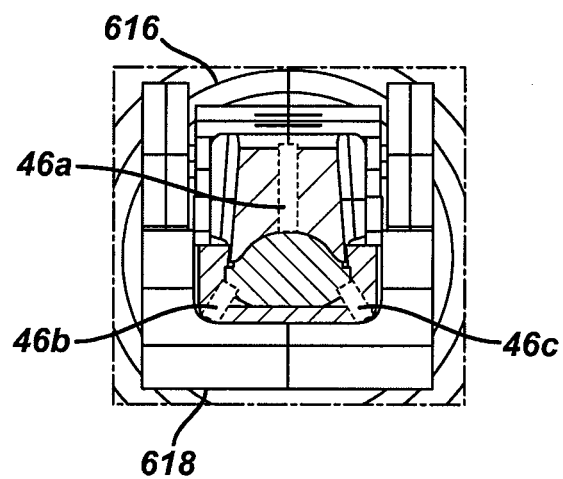
FIG. 14B is a cross-sectional view of another embodiment upper and lower jaws of the tool of FIG. 1 having multiple aspiration holes formed therein.

Additional features to facilitate aspiration of the cut tissue can be formed on the upper and lower jaws. In one exemplary embodiment, one or more aspiration holes, shown in FIGS. 13-14B, can be formed in either or both of the upper and lower jaws 616, 618. The one or more aspiration holes can allow ambient gases and/or fluid to flow therethrough to aid in removing the tissue from the tissue-receiving cavity 630 and into the inner lumen of the elongate shaft 612. The aspiration holes can be formed in various locations on the upper and lower jaws 616, 618. FIG. 13 illustrates one embodiment of upper and lower jaws 616, 618 including a single aspiration hole 44a formed in a middle portion of the upper jaw 616, and single aspiration hole 44b formed in the distal end of the lower jaw 618. FIG. 14A illustrates another exemplary embodiment in which the upper jaw 616 includes a single aspiration hole 45a formed in a middle portion of the upper jaw 616, however the lower jaw 618 includes a first aspiration hole 45b formed in a distal portion of the lower jaw 618 and a second aspiration hole 45c formed in a proximal portion of the lower jaw 618. FIG. 14B illustrates yet another embodiment in which the upper jaw 616 includes a single aspiration hole 46a formed in a middle portion of the upper jaw 616, and the lower jaw 618 includes first and second aspiration holes 46b, 46c formed therein. In this embodiment, the aspiration holes 46b, 46c in the lower jaw 618 are formed in opposed lateral sides thereof and they extend at an angle relative to one another. A person skilled in the art will appreciate, however, that any number of holes can be found in either or both of the upper and lower jaws 616, 618 to aid in aspiration.

Figure 15:
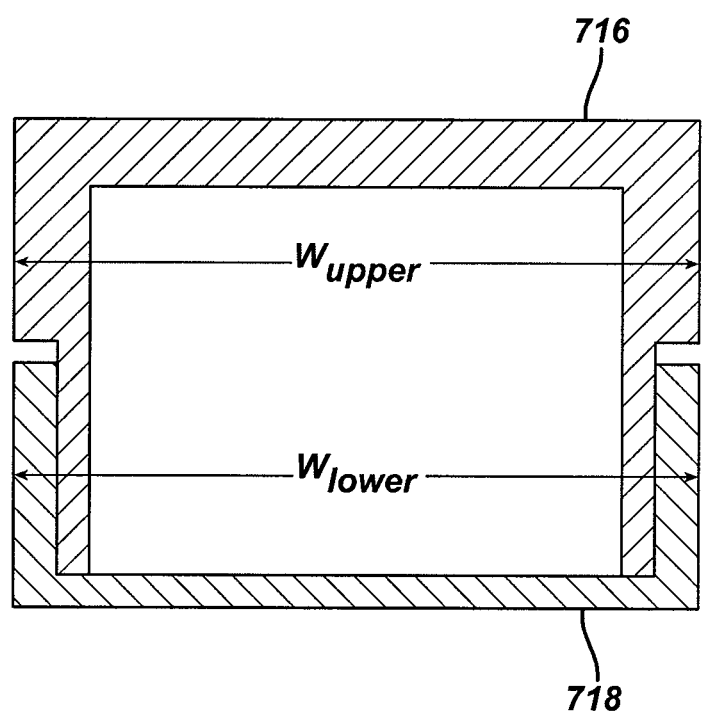
FIG. 15 is a cross-sectional view of another embodiment of upper and lower jaws for use with a spinal disc preparation tool showing the upper jaw having an increased width to minimize cutting of bone surrounding the tissue being cut by the upper and lower jaws.

In another exemplary embodiment, the upper jaw 716 can have a size and shape that is configured to minimize the amount of bone that is scraped by the upper and lower jaws 716, 718 during cutting of the tissue as the bone can clog the tissue-receiving cavity and inner lumen of the elongate shaft. While the upper jaw 716 can have many configurations, in the embodiment illustrated in FIG. 15, an upper portion of the upper jaw 716 has an increased width $W_{upper}$ such that a maximum width of the upper jaw 716 is equal to a maximum width $W_{lower}$ of the lower jaw 718 to minimize scraping of bone surrounding the upper and lower jaws 716, 718. For example, when the upper and lower jaws 716, 718 are used to remove tissue along a surface of a vertebral endplate, the width of the upper jaw 716 can hold the vertebral endplates apart by a distance that is equal to the width of the lower jaw 718. As a result, the risk of scraping the endplates while opening and closing the jaws will be prevented or decreased. A person skilled in the art will appreciate that the upper jaw 716 can have any size and shape that can prevent cutting and scraping of bone as tissue is being cut.

Figure 16A:
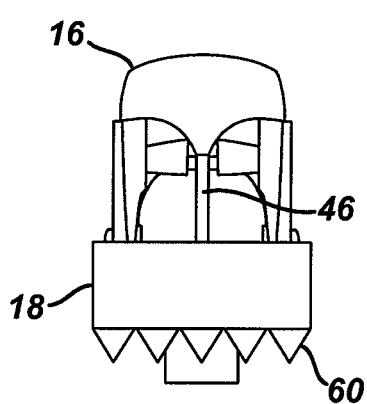
FIG. 16A is a front view of one embodiment of upper and lower jaws having a septum disposed in the lower jaw for dissecting cut tissue.
Figure 16B:
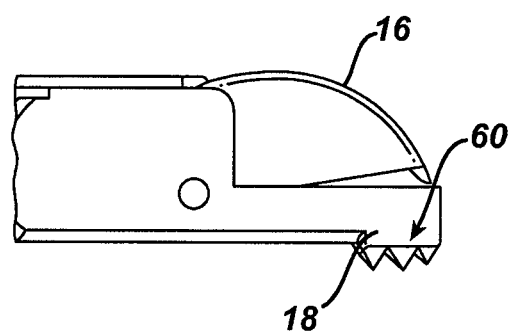
FIG. 16B is a side view of a rasp formed on the lower jaw of FIG. 16A for preparing a vertebral endplate.
Figure 16C:
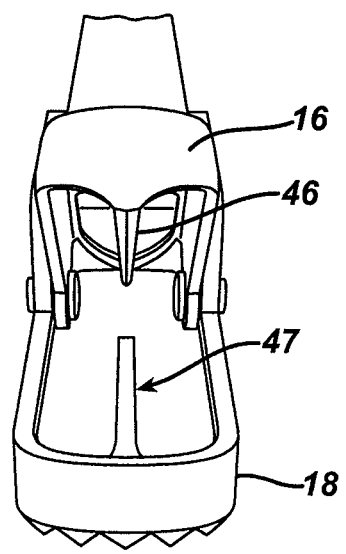
FIG. 16C is a perspective view of the upper and lower jaws of FIG. 16A having the septum and a septum receiver for cutting tissue.

In another exemplary embodiment, either of the upper and lower jaws 16, 18 can include features to decrease the size of the cut tissue to allow for easier passage from the tissue-receiving cavity to the inner lumen of the elongate shaft 12. While this feature can have many configurations, in the embodiment illustrated in FIG. 16A, a septum 46 can be formed in the upper jaw 16 and it can be configured to dissect the cut tissue to facilitate aspiration. The septum 46 can be in the form of an elongate wall or divider extending downwards from the inner surface of the upper jaw 16 and positioned substantially at a midpoint of the upper jaw 16 to facilitate the dissection of the tissue. A person skilled in the art will appreciate that the upper jaw 16 can include more than one elongate wall or divider in order to cut the tissue into even smaller pieces. In another exemplary embodiment, the lower jaw 18 can include a septum receiver 47 for use with the septum 46 to cut tissue. The septum receiver 47 can have a variety of configurations, but in the embodiment illustrated in FIG. 16C, the septum receiver 47 is in the form of an elongate projection extending longitudinally along a midpoint of the inner surface of the lower jaw 18. The septum 46 and the septum receiver 47 are positioned opposite one another such that the two components abut, or the septum 46 is received within a groove or channel in the septum receiver 47, to cut tissue therebetween when the upper jaw 16 is moved toward the lower jaw 18.

In yet another exemplary embodiment, either or both of the upper and lower jaws 16, 18 can include a coating, laminate, sheath, or other covering formed on an inner surface thereof for aiding in the aspiration of cut tissue through the inner lumen. The coating can be formed from a variety of materials, including but not limited to hydrophilic coatings to lubricate the upper and/or lower jaws 16, 18 and hydrophobic coatings such that the coating repels fluid and prevents adhesion of the cut tissue to the inner surface of the upper and/or lower jaws 16, 18. A person skilled in the art will appreciate that any coating, laminate, or sheath can suffice that can facilitate movement of the cut tissue out of the upper and lower jaws 16, 18 and into the inner lumen of the elongate shaft 12. A person skilled in the art will also appreciate that any of the aspiration aides described above can be used in any combination to aid in the aspiration of cut tissue into and through the inner lumen of the elongate shaft 12.

Figure 17A:
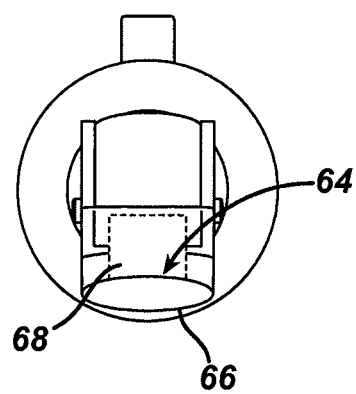
FIG. 17A is a front view of one embodiment of upper and lower jaws including a curette for preparing a vertebral endplate.
Figure 17B:
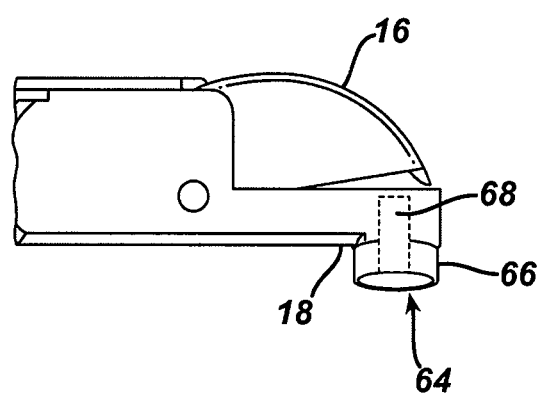
FIG. 17B is a side view of the jaws and curette of FIG. 17A.
Figure 18A:
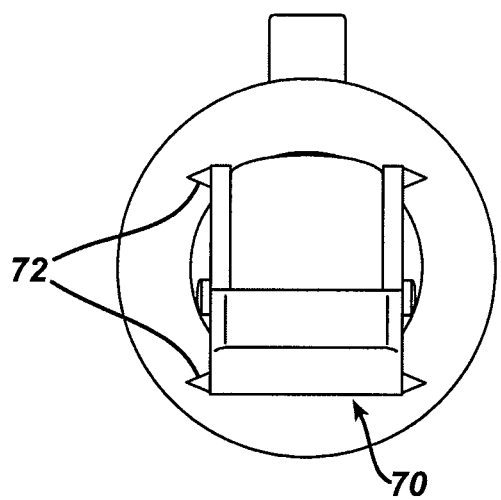
FIG. 18A is a front view of another embodiment of upper and lower jaws including a protrusion and end abraders for preparing a vertebral endplate.
Figure 18B:
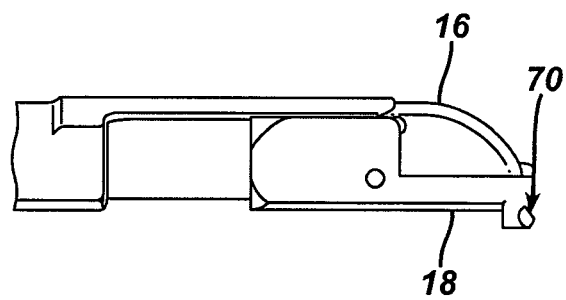
FIG. 18B is a side view of the jaws, protrusion, and end abraders of FIG. 18A.

The upper and lower jaws 16, 18 can also include tissue cutting surface features that can be configured to prepare a vertebral endplate for insertion of an implant between adjacent vertebrae after the removal of the cut tissue. For example, the tissue cutting surface features can be configured to remove tissue along a surface of a vertebral endplate, or they can be adapted to cut into the surface of the vertebral endplate. The tissue cutting surface features can be formed on either or both of the upper and lower jaws 16, 18 and on any location of the jaws 16, 18 in order to facilitate preparation of the endplate. The tissue cutting surface features can also have a variety of configurations. In one exemplary embodiment shown in FIGS. 16A-16B, the tissue cutting surface features are in the form of a rasp 60. The rasp 60 can include a plurality of teeth adapted to remove tissue and cut into the surface of the vertebral endplate. The rasp 60 can include any number of teeth, and the teeth can be formed on any location of the lower jaw 18, although in the illustrated embodiment the teeth are formed on an exterior lower surface thereof. In another exemplary embodiment shown in FIGS. 17A-17B, the tissue cutting surface features are in the form of a curette 64 formed on an exterior surface of the lower jaw 18. The curette 64 is in the form of a cylindrical protrusion 66 formed on the lower jaw 18 that is adapted to cut and/or scrape tissue from vertebral endplates. The protrusion 66 can include an opening 68 therethrough that is in fluid communication with the tissue-receiving cavity formed by the upper and lower jaws 16, 18 to allow the tissue that is cut and/or scraped from the endplate to be aspirated through the tissue-receiving cavity and into the inner lumen of the elongate shaft 12. In another exemplary embodiment, the tissue cutting surface features can be in the form of a protrusion formed on an exterior surface of the lower jaw 18 and adapted to push or pull tissue on the vertebral endplate depending on the shape and angle of the protrusion, as shown in FIGS. 18A-18B. The protrusion 70 is angled away from the distal end of the lower jaw 18 and can thus also scoop the tissue scraped off the vertebral endplate. The upper and lower jaws 16, 18 can also include additional tissue cutting surface features formed at any location thereon. For example, as shown in FIG. 18A, the upper and lower jaws 16, 18 can include one or more 72 edge abraders formed on opposed lateral sides of the upper and lower jaws 16, 18. A person skilled in the art will appreciate that any type of tissue cutting surface features can be formed on the upper and/or lower jaws 16, 18 at any location thereon for preparing vertebral endplates.

In use, the tool 10 can be connected to an aspiration device, for example, by connecting the port 14 to a vacuum that can be activated manually or automatically controlled to aspirate the cut tissue from the tissue-receiving cavity through the inner lumen and out the proximal end of the tool 10. A person skilled in the art will appreciate, however, that the cut tissue can also be passed through the inner lumen without an aspiration device. For example, subsequently cut tissue can push previously cut tissue out of the tissue-receiving cavity and into the inner lumen. The movement of the tissue from the tissue-receiving cavity between the upper and lower jaws through the inner lumen of the elongate shaft can be facilitated by the use of a reduced cross-sectional area in the tissue-receiving cavity, as well as with the additional optional features described above to improve aspiration of the tissue.

The tool 10 can also optionally include features to aid in the collection of the tissue cut by the upper and lower jaws 16, 18. In one exemplary embodiment, the tool 10 can include a tissue collector 50 that can be coupled to the proximal end of the elongate shaft 12 and that can be in fluid communication with the inner lumen of the elongate shaft 12 such that the tissue collector 50 is effective to collect tissue that is cut by the upper and lower jaws 16, 18. The tissue collector 50 can have a variety of configurations, but in one embodiment shown in FIGS. 19A and 20A it can include a housing 52 adapted to couple to the proximal end 12p of the elongate shaft 12. The housing 52 can include an inlet 53 to allow for fluid communication with the inner lumen of the elongate shaft 12, and an outlet 55 to allow for fluid collected in the tissue collector 50 to exit the housing 52. The tissue collector 50 can be coupled to the elongate shaft in a variety of ways. For example, the tissue collector 50 can be removably coupled to the elongate shaft 12, or the tissue collector can be unitary with the elongate shaft 12. While the illustrated embodiment shows a tissue collector 50 configured to couple to the shaft 12 with an in-line configuration, the tissue collector 50 can be located at numerous locations, including separate from the elongate shaft 12 as long as the tissue collector 50 remains in fluid communication with the inner lumen of the elongate shaft 12. In the illustrated embodiment, the tissue collector 50 includes an elongate member 57 that is configured to interlock with an exit port on the inner lumen of the tool 10. The housing 52 can be removably mated to a cap 54 on the elongate member 57 having an o-ring therein. The elongate member 57 can be part of the tool 10, for example, by being formed on the proximal end 12p of the elongate shaft 12, or the elongate member 57 can be a separate component that is removably matable to the elongate shaft 12 and/or the housing 52.

Figure 19A:
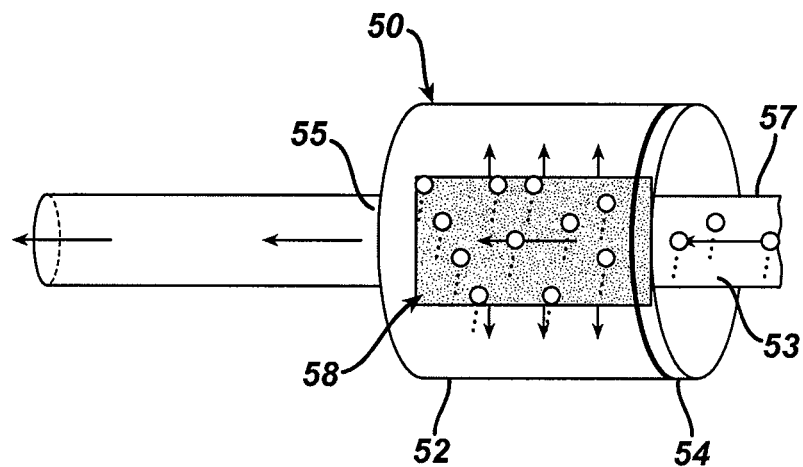
FIG. 19A is a side view of one embodiment of a tissue collector adapted to couple to a spinal disc preparation tool and having a collector module adapted to collect cut tissue therein.
Figure 19B:
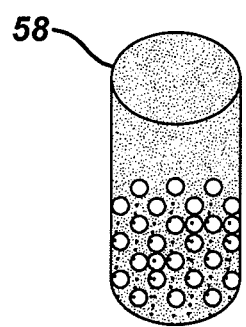
FIG. 19B is a perspective view of the collector module of FIG. 19A including indicia thereon for measuring an amount of cut tissue.
Figure 20A:
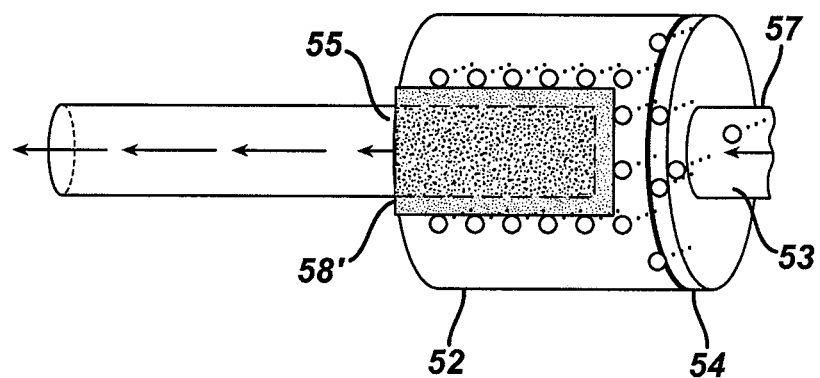
FIG. 20A is a side view of another embodiment of a tissue collector adapted to couple to a spinal disc preparation tool and having a collector module adapted to collect cut tissue on an external surface thereof.
Figure 20B:
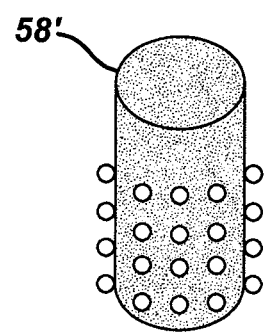
FIG. 20B is a perspective view of the collector module of FIG. 20A including indicia thereon for measuring an amount of cut tissue collected on the outside of the collector module.

The housing 52 can also include a collecting module 58 disposed therein for collecting the cut tissue and separating the cut tissue from other material, such as fluid, that may pass through the inner lumen of the elongate shaft 12. The collector module 58 can be configured to collect tissue in various configuration. In one exemplary embodiment, the collector module 58 can be configured to collect cut tissue therein, as illustrated in FIGS. 19A and 19B. The collector module 58 can thus be configured to be in fluid communication with the inner lumen of the elongate shaft to allow the tissue to travel through the inner lumen and into the collector module 58 through the open end of the collector module 52. The fluid can pass from the collector module 58 into the housing 52 to separate the fluid from the cut tissue, and can exit the housing 52 through the outlet. In another exemplary embodiment, a collector module 58' can be configured to collect tissue on an external surface thereof, as illustrated in FIGS. 20A and 20B. The collector module 58' can thus be configured such that the housing 52 is in fluid communication with the inner lumen of the elongate shaft 12 and receives cut tissue and fluid therefrom. The tissue will collect on the outside of the collector module 58' while the fluid will pass from the housing 52 into the collector module 58' to separate the fluid from the cut tissue, and can then exit the collector module 58' through the outlet formed in the housing 52. Various techniques can be employed to collect the cut tissue. For example, the cut tissue can be collected by removing it from the outside of the collector module 58' or the cut tissue can be collected by inverting the collector module 58' to contain the cut tissue therein.

Figure 21:
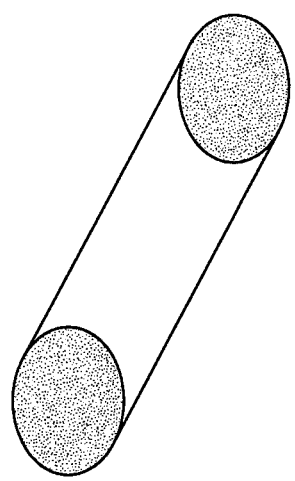
FIG. 21 is a perspective view of one embodiment of a collector module for use with a tissue collector.
Figure 22:
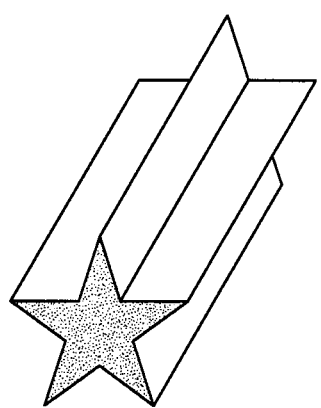
FIG. 22 is a perspective view of another embodiment of a collector module for use with a tissue collector.

The collecting module 58 can have any shape and size adapted to fit inside the housing 52 and collect tissue, and it can be made from any material that facilitates collection of the cut tissue while allowing any fluid to be separated therefrom. For example, the collecting module 58 can be in the form of a mesh bag having an open end with the mesh including holes therein that are sized and shaped to allow fluid but not the cut tissue to pass therethrough. In order to increase the surface area of the collecting module 58 to increase the amount of tissue that can be collected therein or thereon, the collecting module 58 can have a variety of cross-sectional shapes. FIGS. 21-22 illustrate various examples of cross sections of the collecting module 58 that can be used to increase the surface area across which fluid can flow, including an angled cross section shown in FIG. 21, or a star-shaped cross-section shown in FIG. 22. A person skilled in the art will appreciate that the collecting module can have any cross section that can facilitate passage of fluid therethrough, including but not limited to pleats or flutes.

The collecting modules 58 and 58' can also include features adapted to measure the amount of cut tissue collected therein. For example, the collecting modules 58 can include indicia for measuring the amount of tissue collected therein, as shown in FIG. 19B, or for measuring the amount of tissue collected on an external surface of the collecting module 58', as shown in FIG. 20B.

The present invention also provides methods for cutting tissue. In one exemplary embodiment, the distal end of the elongate shaft 12 of the tool 10 can be inserted into the disc space between adjacent vertebrae for cutting the tissue therebetween, for example, a spinal disc which can be removed to be replaced with a spinal disc implant. The distal end of the elongate shaft can be positioned adjacent to the tissue to be cut such that the upper and lower jaws 16, 18 are placed adjacent the tissue. A distal portion of the elongate shaft 12 can also be articulated to help facilitate positioning of the upper and lower jaws 16, 18 relative to the tissue. The actuator 22 pivotally coupled to the handle 20 of the tool 10 can be actuated to cause the upper jaw 16 to move and pivot relative to the lower jaw 18 to cut tissue therebetween. Either using an aspiration device coupled to the tool 10, the force of previously cut tissue pushing subsequently cut tissue, or both, the cut tissue is moved from the tissue-receiving cavity formed between the upper and lower jaws 16, 18 into the inner lumen of the elongate shaft 12. The cut tissue moves proximally through the inner lumen until it either exits the proximal end of the tool 10 or is collected in the tissue collector 50 associated with a proximal end of the elongate shaft 12 and in fluid communication with the inner lumen. The cut tissue can be collected either inside or on the outside of the collector module housed inside the housing of the tissue collector, and can be measured if the collector module includes indicia thereon. As the tissue is being cut and removed, for example from the disc space between adjacent vertebrae, one or more tissue cutting surface features formed on the upper and/or lower jaws 16, 18 can be utilized to cut the vertebral endplates or scrape tissue therefrom to prepare the endplates for insertion of a spinal disc implant into the disc space between the adjacent vertebrae.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A spinal disc preparation tool, comprising:
    an elongate shaft having an inner lumen extending therethrough along a longitudinal axis between proximal and distal ends thereof;
    a lower jaw located on a distal end of the elongate shaft for receiving tissue and delivering tissue to the inner lumen;
    an upper jaw pivotally movable relative to the lower jaw; and
    a handle coupled to a proximal end of the elongate shaft, the handle having formed therein an aspiration hole in fluid communication with the inner lumen;
    wherein the aspiration hole is positioned such that the aspiration hole is blocked by a portion of a monolithic actuator handle when the actuator handle is actuated, the actuator handle being pivotally coupled to an actuator shaft coupled to the upper jaw for pivoting the upper jaw relative to the lower jaw; and
    wherein the upper jaw includes one or more holes formed in a top surface thereof and the lower jaw includes one or more holes formed in a bottom surface thereof, the holes in the upper and lower jaws allowing gas to pass therethrough to aid in aspiration of cut tissue through the inner lumen.

2. The tool of claim 1, wherein the upper and lower jaws define a tissue receiving cavity having a maximum cross-sectional area taken transverse to the longitudinal axis that is less than a cross-sectional area of the inner lumen of the elongate shaft taken transverse to the longitudinal axis at a distal opening of the inner lumen, the cross-sectional area of the tissue-receiving cavity being about 50% less than the cross-sectional area of the inner lumen at the distal opening of the inner lumen.

3. The tool of claim 2, wherein the inner lumen has a cross-sectional area taken transverse to the longitudinal axis that increases from the distal opening to a proximal end of the inner lumen.

4. The tool of claim 3, wherein the cross-sectional area at the proximal end of the inner lumen is about twice the cross-sectional area at the distal opening of the inner lumen.

5. The tool of claim 1, wherein at least one of the upper jaw and lower jaw include an inner surface having a coating for aiding in aspiration of cut tissue through the inner lumen.

6. The tool of claim 5, wherein the coating is hydrophilic and provides a lubricated surface within at least one of the upper jaw and lower jaw.

7. The tool of claim 5, wherein the coating is hydrophobic such that the coating repels fluid and prevents adhesion of cut tissue to the upper jaw and lower jaw.

8. The tool of claim 1, wherein the actuator shaft extends along an external surface of the elongate shaft.

9. The tool of claim 1, further comprising a tissue collection housing coupled to the proximal end of the elongate shaft and in fluid communication with the inner lumen, the tissue collection housing having a tissue collector disposed therein and configured to separate cut tissue from fluid.

10. The tool of claim 1, further comprising at least one bone cutting element formed on at least one of the upper and lower jaws.

11. The tool of claim 1, further comprising a cutting septum formed in the upper jaw and configured to cut and separate cut tissue into two portions.

12. The tool of claim 1, wherein the elongate shaft includes an articulating joint formed therein for allowing angular articulation of the distal end of the shaft.

13. The tool of claim 1, wherein at least one of the upper and lower jaws has a first portion that is pivotally coupled to the elongate shaft or to the actuator shaft, and a second portion that is removably and replaceably coupled to the first portion, the second portion having a cutting blade formed thereon.

14. The tool of claim 1, wherein the upper jaw has a width that is equal to or greater than a width of the lower jaw.

15. The tool of claim 1, further comprising a tissue collection housing coupled to the proximal end of the elongate shaft and in fluid communication with the inner lumen, the tissue collection housing having a tissue collecting module disposed therein and effective to collect tissue cut by the upper and lower jaws, the tissue collection housing including indicia to measure the amount of cut tissue.

16. The tool of claim 1, further comprising a tissue collection housing coupled to the proximal end of the elongate shaft and in fluid communication with the inner lumen, the tissue collection housing having a tissue collecting module disposed therein and effective to collect tissue cut by the upper and lower jaws, the tissue collecting module comprising a mesh bag configured to collect cut tissue therein.

17. The tool of claim 1, further comprising a tissue collection housing coupled to the proximal end of the elongate shaft and in fluid communication with the inner lumen, the tissue collection housing having a tissue collecting module disposed therein and effective to collect tissue cut by the upper and lower jaws, the tissue collecting module comprising a mesh bag configured to collect cut tissue on an external surface thereof.

18. The tool of claim 1, further comprising a tissue collection housing coupled to the proximal end of the elongate shaft and in fluid communication with the inner lumen, the tissue collection housing having a tissue collecting module disposed therein and effective to collect tissue cut by the upper and lower jaws, the tissue collection housing being removably coupled to the elongate shaft.

19. The tool of claim 1, further comprising at least one tissue cutting surface feature formed on at least one of the upper and lower jaws.

20. A spinal disc preparation tool, comprising:
an elongate shaft having an inner lumen extending therethrough along a longitudinal axis between proximal and distal ends thereof;
a lower jaw disposed on the distal end of the elongate shaft;
an actuator shaft extending along an external surface of the elongate shaft and coupled to an upper jaw for pivoting the upper jaw relative to the lower jaw, the upper jaw being movable relative to the lower jaw to cut tissue therebetween and deliver tissue to the inner lumen of the elongate shaft; and
a handle coupled to a proximal end of the actuator shaft, the handle having formed therein an aspiration hole in fluid communication with the inner lumen;
wherein the aspiration hole is positioned such that the aspiration hole is blocked by a portion of a monolithic actuator handle when the actuator handle is actuated, the actuator handle being pivotally coupled to the actuator shaft; and
wherein at least one of the upper and lower jaws has a proximal portion that is pivotally coupled to the elongate shaft or to the actuator shaft, and a distal portion that is removably and replaceably coupled to the proximal portion, the distal portion having a cutting blade formed thereon.

21. The tool of claim 20, wherein the distal portion comprises a removable hood having the cutting blade formed thereon for cutting tissue.

22. The tool of claim 20, wherein the distal portion comprises a removable insert having the cutting blade formed thereon for cutting tissue.

23. The tool of claim 20, wherein the proximal portion includes a mating element formed thereon for mating with a complementary mating element formed on the distal portion.

* * * * *